US00PP25442P2

(12) United States Plant Patent
Valin

(10) Patent No.: US PP25,442 P2
(45) Date of Patent: Apr. 14, 2015

(54) *DIGITALIS* PLANT NAMED 'DG 09/4'

(50) Latin Name: ***Digitalis* hybrid**
Varietal Denomination: DG 09/4

(71) Applicant: Charles Valin, Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 142 days.

(21) Appl. No.: 13/986,481

(22) Filed: May 7, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new cultivar of *Digitalis* plant named 'DG 09/4' that is characterized by flowers having petals with an outer surface colored dark pink with apricot tinges and an inner surface colored yellow with orange tinges and dark pink margins, deeply serrated leaves, continuous flowering and sterile flowers.

1 Drawing Sheet

Botanical classification: *Digitalis* hybrid.
Variety denomination: 'DG 09/4'.

BACKGROUND OF THE INVENTION

The present invention relates to a new and distinct cultivar of *Digitalis* plant botanically known as *Digitalis* hybrid and hereinafter referred to by the cultivar name 'DG 09/4'.

'DG 09/4' originated from the crossing of the female or seed parent a proprietary *Digitalis purpurea* identified as 'DG05006' (not patented) and the male or pollen parent a proprietary *Digitalis canariensis* identified as 'DG05043' (not patented). The crossing was conducted in the Summer of 2008 in Harkstead, Ipswich, United Kingdom. The resulting seeds were subsequently planted and grown. The cultivar 'DG 09/4' was selected by the inventor in the Summer of 2009 in a controlled environment as a single plant within the progeny of the stated cross in a cultivated area of Harkstead, Ipswich, United Kingdom.

Asexual reproduction of the new cultivar 'DG 09/4' first occurred by terminal cuttings in the Summer of 2009 in Harkstead, Ipswich, United Kingdom. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Digitalis* cultivar 'DG 09/4'. These traits in combination distinguish 'DG 09/4' as a new and distinct cultivar apart from other existing known varieties of *Digitalis*.

1. *Digitalis* 'DG 09/4' exhibits continuous flowering.
2. *Digitalis* 'DG 09/4' is sterile.
3. *Digitalis* 'DG 09/4' exhibits flowers having petals with an outer surface colored dark pink with apricot tinges and an inner surface colored yellow with orange tinges and dark pink margins.
4. *Digitalis* 'DG 09/4' exhibits deeply serrated leaves.

The closest comparison cultivar is *Digitalis* 'Waldigone' (U.S. Plant Pat. No. 20,937). 'DG 09/4' is distinguishable from 'Waldigone' by the following characteristics:

1. *Digitalis* 'DG 09/4' exhibits flowers having petals with an outer surface colored dark pink with apricot tinges and an inner surface colored yellow with orange tinges and dark pink margins. The flowers of 'Waldigone' are yellow with tinges of orange and red.
2. *Digitalis* 'DO 09/4' exhibits deeply serrated leaves. The leaves of 'Waldigone' are slightly serrated.

'DG 09/4' is distinguishable from the female parent 'DG05006' by the following characteristics:

1. 'DG 09/4' exhibits flower petals having a dark pink outer surface with apricot tinges. The flower petals of 'DG05006' have an outer surface that is lighter pink in color.
2. 'DG 09/4' exhibits sterile flowers. The flowers of 'DG05006' produce seeds.
3. 'DG 09/4' exhibits continuous flowering. The flowers of 'DG05006' produce one flush per season.
4. 'DG 09/4' exhibits deeply serrated leaves. The leaves of 'DG05006' are slightly serrated.

'DG 09/4' is distinguishable from the male parent 'DG05043' by the following characteristics:

1. 'DG 09/4' exhibits flower petals having a dark pink outer surface with apricot tinges. The flower petals of 'DG05043' have an outer surface that is orange in color.
2. 'DG 09/4' exhibits sterile flowers. The flowers of 'DG05043' produce seeds.
3. 'DG 09/4' exhibits continuous flowering. The flowers of 'DG05043' produce one flush per season.

BRIEF DESCRIPTION OF THE DRAWING

The accompanying photograph illustrates the distinguishing traits of *Digitalis* 'DG 09/4'. The plant in the photograph shows an overall view of a 10 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Digitalis* cultivar named 'DG 09/4'. Data was collected in Mainz, Germany from 10 month plants grown outdoors in 25 cm. diameter containers. The time of year was Autumn and the temperature range was 10-16 degrees Centigrade during the day and 5-10 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'DG 09/4' has not been tested under all possible conditions and phenotypic differences may be observed with variations in environmental, climatic, and cultural conditions, however, without any variance in genotype.

Botanical classification: *Digitalis* hybrid 'DG 09/4'.
Annual or perennial: Perennial.
Parentage: 'DG 09/4' is the product of the female or seed parent *Digitalis purpurea* 'DG05006' and the male or pollen parent *Digitalis canariensis* 'DG05043'.
Plant type: Herbaceous perennial.
Vigor: Strong.
Growth habit: Upright.
Plant shape: Bushy, upright.
Suitable container size: 25 cm. pots.
Height: 50 cm. in height.
Width: 50 cm. in width.
Low temperature tolerance: −10° Centigrade.
High temperature tolerance: 35° Centigrade.
Propagation: Terminal cuttings or tissue culture.
Crop time: Approximately 5 months.
Root system: Fine and fibrous.
Stem:
- *Basal branching.*—Yes.
- *Average number of lateral branches.*—12.
- *Pinching.*—Yes.
- *Lateral branch diameter.*—5 mm. in diameter.
- *Lateral branch length.*—30 cm. in length.
- *Internode length.*—15 mm.
- *Stem shape.*—Round.
- *Stem strength.*—Strong.
- *Stem color.*—190A.
- *Pubescence.*—Present.

Foliage:
- *Leaf arrangement.*—Alternate.
- *Compound or single.*—Single.
- *Number of leaves per lateral branch.*—20 to 25.
- *Leaf shape.*—Elliptic.
- *Leaf apex.*—Apiculate.
- *Leaf base.*—Attenuate.
- *Leaf length.*—22 cm. in length.
- *Leaf width.*—10 cm. in width.
- *Texture.*—Glabrous both surfaces.
- *Pubescence.*—Both sides covered with short hairs.
- *Leaf margin.*—Deeply serrated.
- *Venation pattern.*—Lacinate.
- *Young leaf color (upper surface).*—N137B.
- *Young leaf color (lower surface).*—138A.
- *Mature leaf color (upper surface).*—N137A.
- *Mature leaf color (lower surface).*—138A.
- *Vein color (upper surface).*—138C.
- *Vein color (under surface).*—138D.
- *Leaf attachment.*—Petiolate.
- *Petiole dimensions.*—3 mm. in length, and 0.8 mm. in diameter.
- *Petiole color.*—138D.
- *Durability of foliage to stress.*—Strong.

Flower:
- *Inflorescence arrangement.*—Raceme.
- *Inflorescence dimensions.*—30 to 35 cm. in length and 7 cm. in width.
- *Flower type.*—Single bilabiate campanulate.
- *Quantity of flowers per lateral stem.*—20.
- *Quantity of flower buds per lateral stem.*—5.
- *Quantity of flowers and buds per plant.*—150 to 300.
- *Natural flowering season.*—May to frost.
- *Time to flower.*—4 months.
- *Rate of flower opening.*—Continuous.
- *Fragrance.*—Absent.
- *Flower bud length.*—2 cm.
- *Flower bud diameter.*—8 mm.
- *Flower bud shape.*—Tubular.
- *Bud color.*—145C, tip 59A.
- *Rate of bud opening.*—3 to 4 days.
- *Flower aspect.*—Outward.
- *Flower shape.*—Bilabiate campanulate.
- *Flower dimensions.*—3.5 cm. in diameter and 4.0 cm. in height.
- *Flower longevity.*—7 days.
- *Number of petals.*—5.
- *Fused or unfused.*—Fused.
- *Petal arrangement.*—Campanulate with five fused petals.
- *Petal texture.*—Outer surface has very short hairs, inner surface hirsute on lip.
- *Petal shape.*—Fused becoming campanulate.
- *Petal margin.*—Entire.
- *Petal apex.*—Ovate.
- *Petal base.*—Fused.
- *Petal length.*—Upper petal 4.0 cm, lower lip petal 4.2 cm.
- *Petal width.*—Upper and lower petals 1.7 cm.
- *Petal color when opening (upper side).*—185B, base 8C, lower petals spotted 187A.
- *Petal color when opening (under side).*—8C, tip blushed 185B, lower lip spotted 187A.
- *Petal color fully opened (upper side).*—184D, blushed with 179D, lower petals spotted 187A.
- *Petal color fully opened (under side).*—18C, tip blushed 169C, margin 184D, lower lip spotted 187A.
- *Petal color fading to.*—Not fading.
- *Self-cleaning or persistent.*—Self-cleaning.

Sepals:
- *Sepal arrangement.*—Not fused.
- *Number of sepals.*—5.
- *Sepal shape.*—Lanceolate.
- *Sepal margin.*—Entire.
- *Sepal apex.*—Acuminate.
- *Sepal base.*—Cuspidate.
- *Sepal dimensions.*—1.5 cm. in length and 6 mm. in width.
- *Young sepal color (upper side).*—145A.
- *Young sepal color (under side).*—145A.
- *Mature sepal color (upper side).*—137C.
- *Mature sepal color (under side).*—137C.

Peduncle:
- *Peduncle dimensions.*—20 cm. in length and 5 mm. in diameter.

*Peduncle angle.*—0 degrees from stem.
*Peduncle strength.*—Strong.
*Peduncle color.*—137C, blushed 187A.

Pedicels:

*Pedicel dimensions.*—1 cm. in length and 2 mm. in diameter.
*Pedicel strength.*—Strong.
*Pedicel color.*—145A, with base 187A.

Reproduction organs:

*Stamen number.*—4.
*Anther shape.*—Reniform.
*Anther length.*—4.0 mm.
*Anther color.*—4A, turning 166C.
*Amount of pollen.*—Moderate.
*Pollen color.*—4D.
*Pistil number.*—1.
*Pistil length.*—3.0 cm.
*Stigma shape.*—Bifid.
*Stigma color.*—18C.
*Style length.*—2.2 cm.
*Style color.*—184D.
*Ovary color.*—145AD.

Fruit: Fruit shape: Ovoid.

*Fruit dimensions.*—8 mm. in length and 5 mm. in diameter.
*Fruit color.*—137C.

Seeds: None, sterile.

Disease and pest resistance: Disease and pest resistance has not been observed.

The invention claimed is:

1. A new and distinct variety of *Digitalis* plant named 'DG 09/4' as described and illustrated.

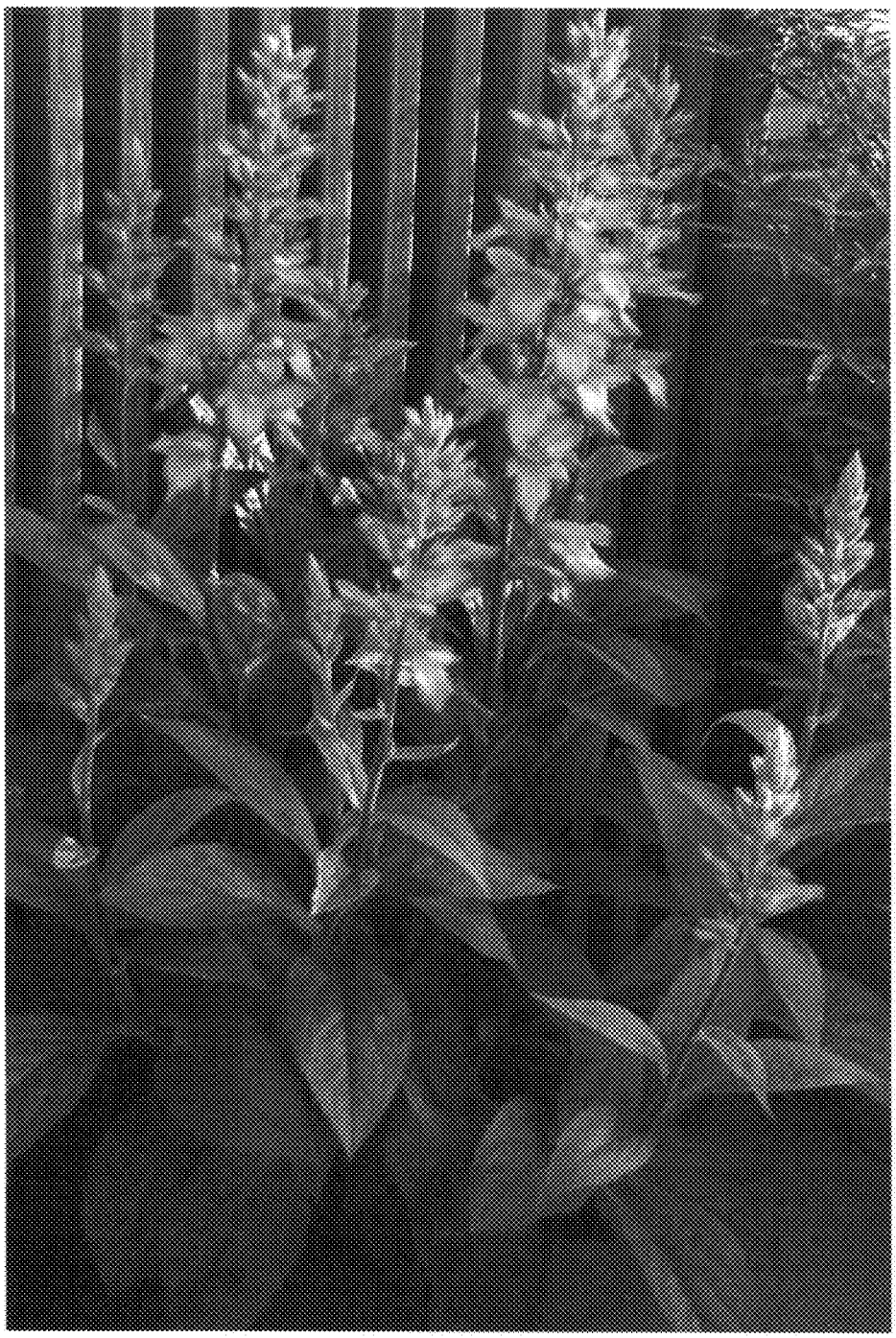

* * * * *